United States Patent
Irwin et al.

(10) Patent No.: US 11,894,118 B2
(45) Date of Patent: Feb. 6, 2024

(54) METHOD OF AUTHENTICATING CONTROLLED-SUBSTANCE TRANSACTIONS

(71) Applicant: CENTURION MANAGEMENT GROUP, INC., Greenville, SC (US)

(72) Inventors: Lawrence Richard Irwin, Greenville, SC (US); Timothy Leroy Polin, Greer, SC (US)

(73) Assignee: CENTURION MANAGEMENT GROUP, INC., Greenville, SC (US)

( * ) Notice: Subject to any disclaimer, the term of this patent is extended or adjusted under 35 U.S.C. 154(b) by 137 days.

(21) Appl. No.: 17/253,211

(22) PCT Filed: Jun. 17, 2019

(86) PCT No.: PCT/US2019/037474
§ 371 (c)(1),
(2) Date: Dec. 17, 2020

(87) PCT Pub. No.: WO2019/245964
PCT Pub. Date: Dec. 26, 2019

(65) Prior Publication Data
US 2021/0280289 A1 Sep. 9, 2021

Related U.S. Application Data (60) Provisional application No. 62/686,958, filed on Jun. 19, 2018.

(51) Int. Cl.
*G16H 20/13* (2018.01)
*G16H 70/40* (2018.01)
(Continued)

(52) U.S. Cl.
CPC ............ *G16H 20/13* (2018.01); *A61J 7/0076* (2013.01); *G06Q 10/0832* (2013.01);
(Continued)

(58) Field of Classification Search
CPC ........ A61J 7/00; A61J 7/0076; G06Q 10/083; G06Q 10/08; G06Q 10/0832;
(Continued)

(56) References Cited

U.S. PATENT DOCUMENTS

| 6,952,681 B2 | 10/2005 | McQuade |
| 8,355,992 B1 | 1/2013 | Haugh |

(Continued)

FOREIGN PATENT DOCUMENTS

| WO | 2007133478 A2 | 11/2007 | |
| WO | WO-2016069304 A1 * | 5/2016 | ............... A61J 1/03 |
| WO | 2016172516 A1 | 10/2016 | |

OTHER PUBLICATIONS

Aventure and BIO-key® International, Inc. Partner to provide Biometric Solution for Electronic Prescribing of Controlled Substances; PRWeb Newswire Apr. 9, 2015; NA (Year: 2015).*

(Continued)

*Primary Examiner* — Hiep V Nguyen
(74) *Attorney, Agent, or Firm* — Timothy D. St. Clair; Parker Poe Adams & Bernstein LLP (57) ABSTRACT

A method for authenticating a transaction of a controlled substance. The method may include providing a computer-implemented data repository, providing a governing body to approve distributors to form a network of distributors, communicating governing body data, communicating controlled substance distributor data, and communicating distributor administrator data, distributor employee data, and controlled substance recipient data all to the computer-implemented data repository. The method may further include executing a controlled substance transaction for a controlled substance amount, in which different steps of the transaction are unlocked upon confirmation of an identity of an authorized individual associated with a distributor and/or confirmation of an identity of a recipient and the requested (Continued)

amount of controlled substance plus the amount of controlled substance the recipient has previously received during a predetermined time interval, which is compared with the governing body's controlled substance amount limit. The transaction may proceed or end based on the comparison.

13 Claims, 6 Drawing Sheets

(51) Int. Cl.
*A61J 7/00* (2006.01)
*G06Q 10/0832* (2023.01)
*G06Q 10/0833* (2023.01)
*G06Q 50/22* (2018.01)

(52) U.S. Cl.
CPC ......... *G06Q 10/0833* (2013.01); *G06Q 50/22* (2013.01); *G16H 70/40* (2018.01)

(58) Field of Classification Search
CPC .... G06Q 10/0833; G06Q 50/22; G16H 20/13; G16H 70/00; G16H 70/40
USPC .......................................................... 705/2
See application file for complete search history.

(56) References Cited

U.S. PATENT DOCUMENTS

| | | | |
|---|---|---|---|
| 8,626,529 B1* | 1/2014 | Pinsonneault | G06Q 10/0635 |
| | | | 705/2 |
| 8,725,532 B1 | 5/2014 | Ringold | |
| 2002/0042762 A1* | 4/2002 | McQuade | G06Q 10/08 |
| | | | 705/29 |
| 2003/0225596 A1 | 12/2003 | Richardson | |
| 2004/0225528 A1 | 11/2004 | Brock | |
| 2007/0260491 A1 | 11/2007 | Palmer | |
| 2010/0299158 A1 | 11/2010 | Siegel | |
| 2011/0166878 A1 | 7/2011 | Louie | |
| 2014/0074283 A1* | 3/2014 | Blackburn | A61J 7/0076 |
| | | | 700/237 |
| 2016/0171164 A1* | 6/2016 | Kinzer | G16H 40/67 |
| | | | 705/3 |
| 2016/0180058 A1 | 6/2016 | Reardan et al. | |
| 2017/0112181 A1* | 4/2017 | Belfance | B65B 5/04 |
| 2017/0199984 A1 | 7/2017 | Lohman | |

OTHER PUBLICATIONS

Aventura and BIO-key(R) International, Inc. Partner to Provide Biometric Solution for Electronic Prescribing of Controlled Substances ;: PRWeb Newswire Apr. 9, 2015: NA. (Year: 2015).*
International Search Report for US2019037474, dated Aug. 29, 2019.

* cited by examiner

METHOD OF AUTHENTICATING CONTROLLED-SUBSTANCE TRANSACTIONS

CROSS-REFERENCE TO RELATED APPLICATION

This application claims the priority benefit of Provisional U.S. Patent Application Ser. No. 62/686,958 filed on Jun. 19, 2018, the entire scope and content of which are hereby incorporated herein by reference.

TECHNOLOGICAL FIELD

The present invention relates generally to the field of controlled substance distribution. More particularly, the present invention relates to a method for authenticating and controlling transactions and/or exchanges of a controlled substance via a network of distributors.

DESCRIPTION OF THE RELATED ART

In the field of controlled substance distribution there is a need to monitor the eligibility of a recipient to receive the controlled substance and the amount of controlled substance a recipient might receive. Current methods of such monitoring are often inefficient, inexact, and allow recipients to manipulate, overcome, and/or defeat the current methods, for a disallowed outcome, because the controlled substance transaction is not properly monitored, authenticated, and/or controlled among distributors.

Certain controlled substances, for example cannabis, have been legalized in more jurisdictions, and therefore an additional need has arisen for an efficient and reliable method for authenticating and controlling controlled substance transactions and/or exchanges.

BRIEF SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention; its sole purpose is to present concepts of the invention in a simplified form as a prelude to the more detailed description that is subsequently presented.

The present invention includes a method for controlling the transfer or dispensing of a controlled substance via a network of distributors. In one embodiment of the invention, the method includes providing a computer-implemented data repository both to send and to receive information. The information may include the data of a governing body of the controlled substance, the data of the distributor or distributors of a controlled substance, and the data of a recipient or recipients of a controlled substance. The method may further include the step of providing a controlled substance governing body to approve distributors of a controlled substance to form a network of distributors of the controlled substance. The method may include communicating, to the data repository, data of a governing entity including the controlled substance distributor data, which may also include distinct distributor program identification numbers for each approved distributor.

Controlled substance distributor data may also be communicated to the data repository. In one embodiment, the controlled substance distributor data may include distributor administrator data for each approved distributor, such as an administrator program identification number and an administrator biometric, and distributor individual data, such as a stored identification number and stored biometric data regarding an authorized individual associated with a distributor who is authorized and approved to participate in controlled substance transactions. Additionally, recipient data may be communicated to the data repository. In one embodiment, the recipient data may include a stored recipient program identification number and biometric data, a controlled substance amount limit, and a controlled substance total. The controlled substance amount limit may be the total amount of the controlled substance a recipient may receive in any time period or interval pursuant to limits established by a governing body (such as a State legislature or rule-making agency). Further, the controlled substance total may be the total amount of the controlled substance the recipient has already received during any time period or interval.

The method may also include the steps of executing a controlled substance transaction for a specified or predetermined amount of the controlled substance. For example, a controlled substance transaction system may be provided whereby services related to the exchange of the controlled substance may be carried out. In one embodiment, the controlled substance transaction system may include a first barrier, which may be unlocked upon confirmation of the identity of an authorized individual associated with a distributor, and a second barrier, which may be unlocked upon confirmation of the identity of a recipient of the controlled substance. The program identification number of a first individual may be entered and the biometric data of a first individual may be entered regarding an authorized individual associated with a distributor. The identity of the distributor individual may be confirmed by comparing the program identification number and the biometric data entered with the program identification number of the individual and the biometric data of the corresponding distributor individual already stored in the data repository. The first barrier of the controlled substance transaction system may be unlocked only if the entered data matches the stored data.

The recipient program identification number and the recipient biometric data may be entered by the recipient. The identity and eligibility of the recipient may be confirmed by comparing the program identification number and the biometric data entered with the program identification number of the recipient and the biometric data of the corresponding recipient already stored in the data repository. The second barrier of the controlled substance transaction system may be unlocked only if the entered data matches the stored data.

A requested predetermined amount of the controlled substance, including descriptors such as quantity, type, and the like, may be entered into the controlled substance data repository. Further, the controlled substance total amount plus the requested amount of the controlled substance may be compared with a predetermined controlled substance amount limit as established by a governing body. If the sum of the requested quantity of the controlled substance together with previously-provided quantities of the controlled substance is not greater than the controlled substance amount limit as established by the governing body, then the requested amount of the controlled substance may be transferred to the recipient. If the sum is greater than the controlled substance amount limit, then the transaction may be rejected. The controlled substance total may then be updated in accordance with the outcome of the controlled substance transaction and the controlled substance transaction may be recorded in the data repository. In an embodiment of the present invention, the controlled substance may be cannabis based, however other controlled substances may be contemplated.

In an embodiment of the present invention, the method may further include the steps of enrolling the recipient by generating a first recipient program identification number and a first recipient biometric data and communicating the data to the data repository. In some embodiments, the method may include generating a unique recipient card with an expiration date and communicating the expiration date and unique recipient card type to the data repository. In other embodiments, the controlled substance recipient data may include a unique recipient card having an expiration date.

In yet another embodiment of the present invention, the method may include the steps of allowing for the return or surrender of a quantity of controlled substance and of updating the controlled substance total in the computer-implemented data repository to reflect such return or surrender.

In still another embodiment of the present invention, the method may include allowing for the tracking of transfer of the controlled substance among distributors within the network of distributors.

In another embodiment of the present invention, the method may include allowing for the tracking of receipt of the controlled substance among distributors within the network of distributors.

With certain controlled substances, the weight quantity of the substance may change over time, such as by absorption of ambient humidity or by drying. In another embodiment of the present invention, the method may include allowing for the tracking of expansion or shrinkage of the controlled substance, such as among distributors within the network of distributors.

In another embodiment of the present invention, the method may include allowing for the tracking of waste of the controlled substance, such as among distributors within the network of distributors.

In yet another embodiment of the present invention, the computer-implemented data repository may include the controlled substance transaction system.

The present invention further includes a method of executing a controlled substance transaction for a predetermined amount of controlled substance. In one embodiment, the method includes the steps of providing a controlled substance transaction system for executing services related to the exchange of the controlled substance. The controlled substance transaction system may include a first barrier, which may be overcome only upon confirmation of an identity of an authorized individual associated with an authorized distributor, and a second barrier, which may be overcome only upon confirmation of an identity and eligibility of a recipient. The method may further include the steps of entering a first program identification number and a first biometric datum of an authorized individual associated with a distributor and then confirming the identity of that individual by comparing the first program identification number and the first biometric data with the stored program identification number for that individual and the stored biometric data corresponding to that individual. The first barrier may be unlocked only if the first program identification number and the first biometric data match the stored program identification number and the stored biometric data corresponding to that individual associated with a distributor. Additionally, the method may include the steps of entering a first recipient program identification number and a first recipient biometric data of the recipient and then confirming the identity and eligibility of the recipient by comparing the first recipient program identification number and the first recipient biometric data with the stored recipient program identification number and stored biometric data corresponding to the recipient. The second barrier may be unlocked only if the first recipient program identification number and the first recipient biometric data match the stored recipient program identification number and the stored recipient biometric data corresponding to the recipient.

The method may also include the steps of entering a requested amount of the controlled substance and comparing a sum of the controlled substance total and the requested amount of the controlled substance with the controlled substance amount limit. The requested amount of the controlled substance may be transferred to the recipient only if the sum is less than or equal to the controlled substance amount limit. Alternatively, the request may be rejected if the sum is not less than or equal to the controlled substance amount limit.

In an embodiment of the present invention, the method may further include the steps of enrolling the recipient by generating the first recipient program identification number and the first recipient biometric data and communicating the data to the data repository. In some embodiments, the method may include generating a unique recipient card with an expiration date and communicating the expiration date and unique recipient card type to the data repository. In other embodiments, the controlled substance recipient data may include a unique recipient card having an expiration date.

The method for controlling the dispensing of a controlled substance via a network of distributors may alternatively include providing a computer-implemented data repository both to send and to receive information. The information may include the data of a governing body of the controlled substance, the data of the distributor or distributors of a controlled substance, and the data of a recipient or recipients of a controlled substance. The method may further include the step of providing a controlled substance governing body to approve distributors of a controlled substance to form a network of distributors of the controlled substance. The method may include communicating, to the data repository, data of the governing body including the controlled substance distributor data, which may also include distinct distributor program identification numbers for each approved distributor.

Controlled substance distributor data may also be communicated to the data repository. In one embodiment, the controlled substance distributor data may include distributor administrator data for each approved distributor, such as an administrator program identification number and administrator biometric, and distributor personnel data, such as a stored identification number and stored biometric data for individuals associated with the distributor. Additionally, recipient data may be communicated to the data repository. In one embodiment, the recipient data may include a stored recipient program identification number and biometric data, a controlled substance amount limit as set by law, by medical prescription, or by other authority, and a controlled substance total. The controlled substance amount limit may be the total amount of the controlled substance the recipient may receive in any specified time period or time interval. Further, the controlled substance total may be the total amount of the controlled substance the recipient has already purchased during any time period or interval.

The method may also include the steps of executing a controlled substance transaction for an amount of the controlled substance, allowing for return of all or portions of the controlled substance, and allowing for tracking of transfer, receipt, expansion, shrinkage, and/or waste of the controlled substance among distributors within the network of distributors. The controlled substance total may then be updated in accordance with the outcome of the controlled substance transaction and the controlled substance transaction may be recorded in the data repository.

Further features of the present invention will be apparent from the description that follows. After review, such features may in part be disclosed from the description or may be learned by practice of the invention. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The aspects described above, as well as other apparent aspects, advantages, and objectives of the present invention are apparent from the detailed description below in combination with the drawings, in which.

DETAILED DESCRIPTION OF REPRESENTATIVE EMBODIMENTS

The present invention relates to a method for authenticating and controlling a transaction or exchange of a controlled substance. The method may be used to ensure that controlled substances are properly distributed only to individuals authorized and eligible to receive the controlled substances, and limited to an appropriate quantity, the appropriate quantity in some instances being time-dependent. Further, the disclosed process may be used to ensure that the participants in an exchange of a controlled substance are authorized to carry out the requested or proposed exchanges and to do so using a biometric or inherently unique identification as a primary identification and another form of identification as a secondary identifier in order to verify their roles in an exchange. Preferably, a participant's personal identification, such as name, address, and/or social security number are not to be used for identification herein.

Although often described herein as an illustrative embodiment in terms of its use as a method for authenticating and dispensing controlled substances such as cannabis or cannabis based products, it will be clear that the method of the present invention may have various other uses such as with prescription medications, explosives, military equipment, firearms and/or firearm ammunition, vaping fluids, high-valued products such as jewelry and diamonds, and other like products and substances the possession and transfer of which desirably would be controlled and authenticated. In a particular embodiment, for example, the "controlled substance" may be an article of evidence in the custody of a police evidence room, for use in judicial criminal proceedings—the method may be used to ensure that the article of evidence is properly handled and possessed only by individuals authorized and eligible to receive it and that a proper chain of custody of the evidence is created and maintained. Thus, the term "controlled substance" and formatives thereof are defined to include herein any material for which the possession, chain of custody, quantity, usage, and/or timing of possession exchange may desirously be managed.

The method of the present invention involves generally an upstream entity and a downstream entity, the upstream entity being in possession of a controlled substance and the downstream entity being a candidate to whom transfer to and possession of such controlled substance may be considered. With the disclosure herewith provided, various terms may be used to refer to a upstream entity, such as "distributor," "distributor administrator," "distributor personnel," "distributor employee," "authorized individual associated with a distributor," and the like, the context in which each such term is used being indicative of an upstream entity. Similarly, with the disclosure herewith provided, various terms may be used to refer to a downstream entity, such as "recipient" (which in some contexts may be a receiving downstream distributor from an upstream distributor), "customer," "purchaser," "candidate," "candidate recipient," and the like, the context in which each such term is used being indicative of a downstream entity. Thus, in some applications, a second entity denominated as a "downstream entity" with respect to a first entity denominated as an "upstream entity" (in that the second entity receives possession of a controlled substance from the first entity), may thereafter be considered to be an "upstream entity" with respect to a third entity if possession of the controlled substance is subsequently transferred from the second entity as an "upstream entity" to the third entity (which as to such subsequent transfer would be denominated to be a "downstream entity").

Various terms may be considered as constituting what is often referred to herein as a "governing body." For example, with cannabis based products, the "governing body" might be a State government or a regulatory agency that has established, for instance, certain time-based usage limits for the individual consumption of the cannabis based products. As to prescription medications, the "governing body" might be an individual physician who has prescribed the usage limits of the prescription medication for a particular individual, or it might be the original manufacturer of the medication, such as opioids, who is interested in insuring that the full quantities of the medication reach its ultimate intended destinations without portions (or all) of the medication being pilfered at points of transfer between the original manufacturer and the ultimate intended destination. Likewise as to jewelry and diamonds, the "governing body" might be a transferring owner who is interested in protecting the property from theft as it is transferred to a final intended destinations. Regarding explosives, military equipment, firearms and/or firearm ammunition, and other potentially dangerous provisions, the "governing body" might be a State government or a regulatory agency that has established limitations on the manufacture, possession, use, or transfer of such products or, in the case of military equipment, the "governing body" might be the specific military unit charged with responsibility for safekeeping such equipment.

Reference now will be made in detail to embodiments and examples of the present invention. The particular steps recited in these examples, as well as other conditions and details, should not be construed to unduly limit this invention.

The present invention includes a method of authenticating a transaction or exchange of a controlled substance. In one embodiment of the invention, the method includes providing a computer-implemented data repository to both send and receive information. The information may include the data of a governing body of the controlled substance, the data of the distributor or distributors of a controlled substance, and the data of a recipient or recipients of a controlled substance. The method may further include the step of providing a controlled substance governing body to approve distributors of a controlled substance to form a network of distributors of the controlled substance. The method may include communicating, to the data repository, data of the governing body including the controlled substance distributor data, which may also include distinct distributor program identification numbers for each approved distributor.

Controlled substance distributor data may also be communicated to the data repository. In one embodiment, the controlled substance distributor data may include distributor administrator data for each approved distributor, such as an administrator program identification number and administrator biometric, and distributor personnel data, such as a stored identification number and stored biometric data for each authorized individual associated with the distributor. Additionally, recipient data may be communicated to the data repository. In one embodiment, the recipient data may include a stored recipient program identification number and biometric data, a controlled substance amount limit, and a controlled substance total. The controlled substance amount limit may be the total amount of the controlled substance the recipient can purchase in any time period or interval. Further, the controlled substance total may be the total amount of the controlled substance the recipient has already purchased during any specified time period or interval.

The method may also include the steps of executing a controlled substance transaction for a specified amount of the controlled substance. For example, a controlled substance transaction system may be provided whereby services related to the exchange of the controlled substance may be carried out. In one embodiment, the controlled substance transaction system may include a first barrier, which may be overcome only upon confirmation of the identity of an authorized individual associated with a distributor, and a second barrier, which may be overcome only upon confirmation of the identity of a recipient of the controlled substance. The program identification number of a first distributor individual may be entered and the biometric data of a first distributor individual may be entered. The identity of the distributor individual may be confirmed by comparing the program identification number and the biometric data entered with the program identification number of the individual and the biometric data of the corresponding distributor individual already stored in the data repository. The first barrier of the controlled substance transaction system may be overcome only if the entered data matches the stored data.

The recipient program identification number and the recipient biometric data may be entered by the recipient. The identity of the recipient may be confirmed by comparing the program identification number and the biometric data entered with the program identification number of the recipient and the biometric data of the corresponding recipient already stored in the data repository. The second barrier of the controlled substance transaction system may be overcome only if the entered data matches the stored data.

A requested amount of the controlled substance may be entered into the controlled substance data repository. Further, the controlled substance total amount plus the requested amount of the controlled substance may be compared with a controlled substance amount limit. If the sum is less than or equal to the controlled substance amount limit, then the requested amount of the controlled substance may be transferred to the recipient. If the sum is not less than or equal to the controlled substance amount limit, then the transaction may be rejected and the attempted transfer may be recorded. If the controlled substance is transferred, the controlled substance total may then be updated in accordance with the outcome of the controlled substance transaction and the controlled substance transaction may be recorded in the data repository. In an embodiment of the present invention, the controlled substance may be cannabis based, however other controlled substances may be contemplated.

In certain usages of the present invention, the method may further include the steps of enrolling the recipient by generating a first recipient program identification number and a first recipient biometric data and communicating both to the data repository. The method may include generating a unique recipient card, with an expiration date, and communicating the expiration date and unique recipient card type to the data repository. In other embodiments, the controlled substance recipient data may include a unique recipient card having an expiration date.

In yet another embodiment of the present invention, the method may include the steps of allowing for the return of the controlled substance and updating the controlled substance total in the computer-implemented data repository.

In still another embodiment of the present invention, the method may include allowing for the tracking of transfer of the controlled substance among distributors within the network of distributors.

In another embodiment of the present invention, the method may include allowing for the tracking of receipt of the controlled substance among distributors within the network of distributors.

With certain controlled substances, the weight quantity of the substance may change with age, such as by absorption of ambient humidity or by drying. In another embodiment of the present invention, the method may include allowing for the tracking of weight changes of the controlled substance among distributors within the network of distributors.

In another embodiment of the present invention, the method may include allowing for the tracking of waste of the controlled substance among distributors within the network of distributors if, for example, the quantity of the controlled substance is decreased by legitimate spoliation, contamination, spillage, or other loss.

In yet another embodiment of the present invention, the computer-implemented data repository may include the controlled substance transaction system.

The method for controlling the dispensing of a controlled substance via a network of distributors may alternatively include providing a computer-implemented data repository to both send and receive information. The information may include the data of a governing body of the controlled substance, the data of the distributor or distributors of a controlled substance, and the data of a recipient or recipients of a controlled substance. The method may further include the step of providing a controlled substance governing body to approve distributors of a controlled substance to form a network of distributors of the controlled substance. The method may include communicating, to the data repository, data of the governing body including the controlled substance distributor data, which may also include distinct distributor program identification numbers for each approved distributor.

Controlled substance distributor data may also be communicated to the data repository. In one embodiment, the controlled substance distributor data may include distributor administrator data for each approved distributor, such as an administrator program identification number and administrator biometric, and distributor employee data, such as a stored employee identification number and stored employee biometric data. Additionally, recipient data may be communicated to the data repository. In one embodiment, the recipient data may include a stored recipient program identification number and biometric data, a controlled substance amount limit, and a controlled substance total. The controlled substance amount limit may be the total amount of the controlled substance the recipient can purchase in any time period or interval. Further, the controlled substance total may be the total amount of the controlled substance the recipient has already purchased during any time period or interval.

The method may also include the steps of executing a controlled substance transaction for an amount of the controlled substance, allowing for return of the controlled substance, and allowing for tracking of transfer, receipt, expansion, shrinkage, and/or waste of the controlled substance among distributors within the network of distributors. The controlled substance total may then be updated in accordance with the outcome of the controlled substance transaction and the controlled substance transaction may be recorded in the data repository.

The present invention further includes a method of executing a controlled substance transaction for an amount of controlled substance. In one embodiment, the method includes the steps of providing a controlled substance transaction system for executing services related to the exchange of the controlled substance. The controlled substance transaction system may include a first barrier, which may be unlocked only upon confirmation of an identity of an authorized individual associated with a distributor, and a second barrier, which may be unlocked only upon confirmation of an identity of a recipient. The method may further include the steps of entering a first employee program identification number and a first employee biometric data of the distributor employee and then confirming the identity of the distributor employee by comparing the first employee program identification number and the first employee biometric data with the stored employee program identification number and the stored biometric data corresponding to the distributor employee. The first barrier may be unlocked if the first employee program identification number and the first employee biometric data match the stored employee program identification number and the stored employee biometric data corresponding to the distributor employee. Additionally, the method may include the steps of entering a first recipient program identification number and a first recipient biometric data of the recipient and then confirming the identity of the recipient by comparing the first recipient program identification number and the first recipient biometric data with the stored recipient program identification number and stored biometric data corresponding to the recipient. The second barrier may be unlocked only if the first recipient program identification number and the first recipient biometric data match the stored recipient program identification number and the stored recipient biometric data corresponding to the recipient.

The method may also include the steps of entering a requested amount of the controlled substance and comparing a sum of the controlled substance total and the requested amount of the controlled substance with the controlled substance amount limit. The requested amount of the controlled substance may be transferred to the recipient if the sum is less than or equal to the controlled substance amount limit. Alternatively, the request may be rejected if the sum is not less than or equal to the controlled substance amount limit.

In an embodiment of the present invention, the method may further include the steps of enrolling the recipient by generating the first recipient program identification number and the first recipient biometric data and communicating the data to the data repository. In some embodiments, the method may include generating a unique recipient card with an expiration date and communicating the expiration date and unique recipient card type to the data repository. In other embodiments, the controlled substance recipient data may include a unique recipient card having an expiration date.

The accompanying figures illustrate certain of the foregoing aspects of the method of the present invention, as well as additional aspects thereof. The figures represent embodiments of the method of the present invention and are not intended to limit the method of the present invention. In the embodiments of FIGS. 1-4C, the exemplary controlled substance is cannabis as described above; however, other controlled substances, as disclosed hereinabove, are contemplated without departing from the scope of the present invention.

Figure 1:
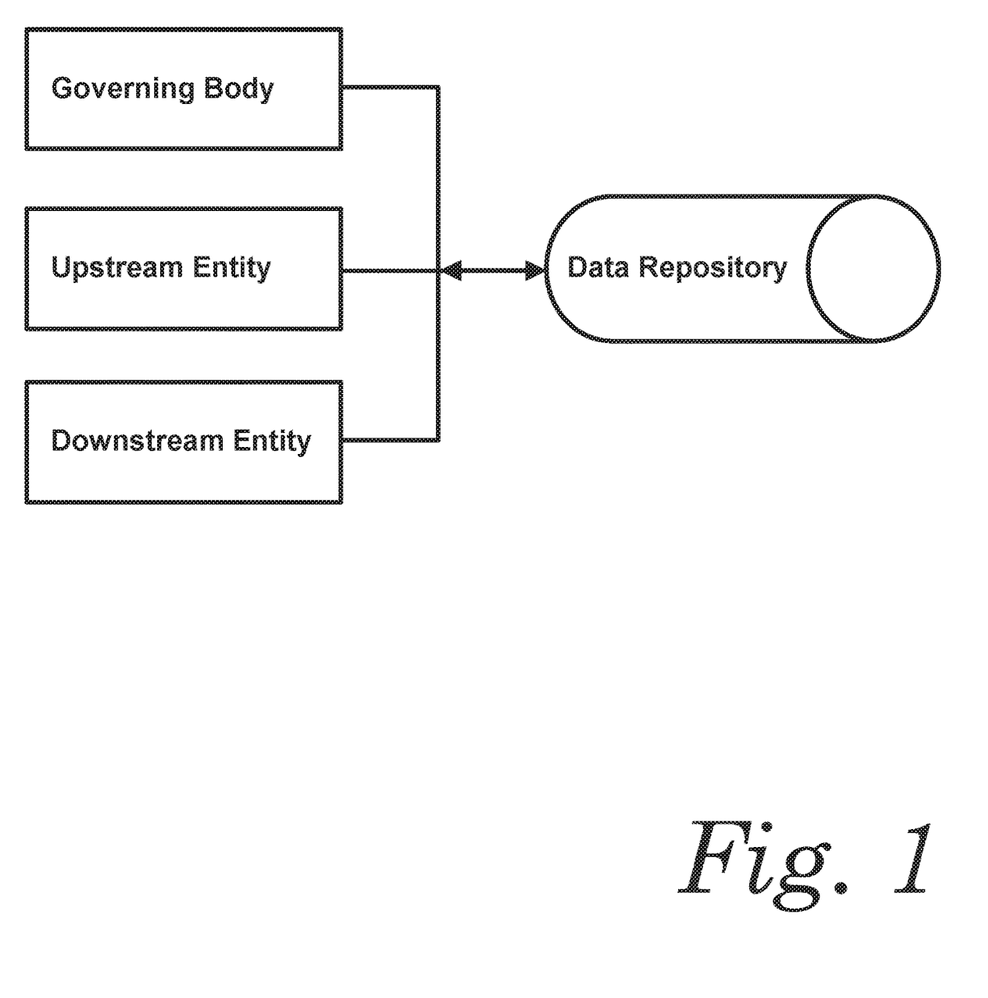
FIG. 1 discloses components of the computer-implemented data repository in accordance with an embodiment of the present invention.

FIG. 1 discloses a flow chart of an embodiment of the basic components of the present invention. For example, the data repository communicates with a controlled substance governing body or bodies, a controlled substance distributor designated as an "upstream entity" in FIG. 1, and a controlled substance recipient designated as a "downstream entity" in FIG. 1.

Figure 2:
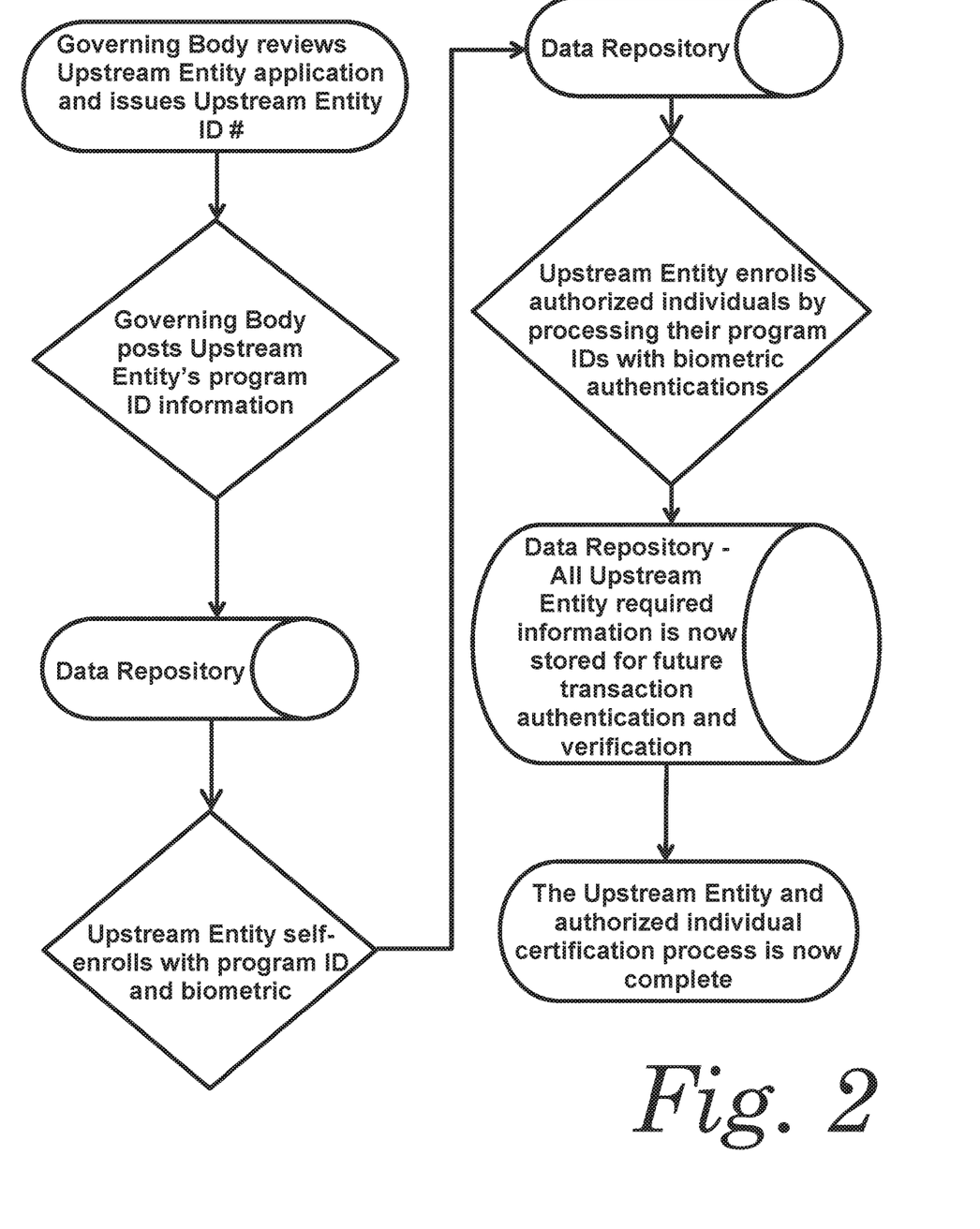
FIG. 2 discloses components of the controlled-substance data repository in accordance with an embodiment of the present invention.

FIG. 2 discloses a flow chart of an embodiment of the approval and enrollment process of a controlled substance distributor, denominated as an "upstream entity" in FIG. 2, by the controlled substance governing body of the present invention. The controlled substance governing board may review a controlled substance distributor application, issue a program identification number, post the program identification information in the computer-implemented data repository such that the distributor administrator may enroll with his or her program identification number and biometric data by communicating this information to the computer-implemented data repository. The distributor administrator may further enroll a distributor employee by communicating the employee program identification number or numbers and biometric data to the computer-implemented data repository.

Figure 3:
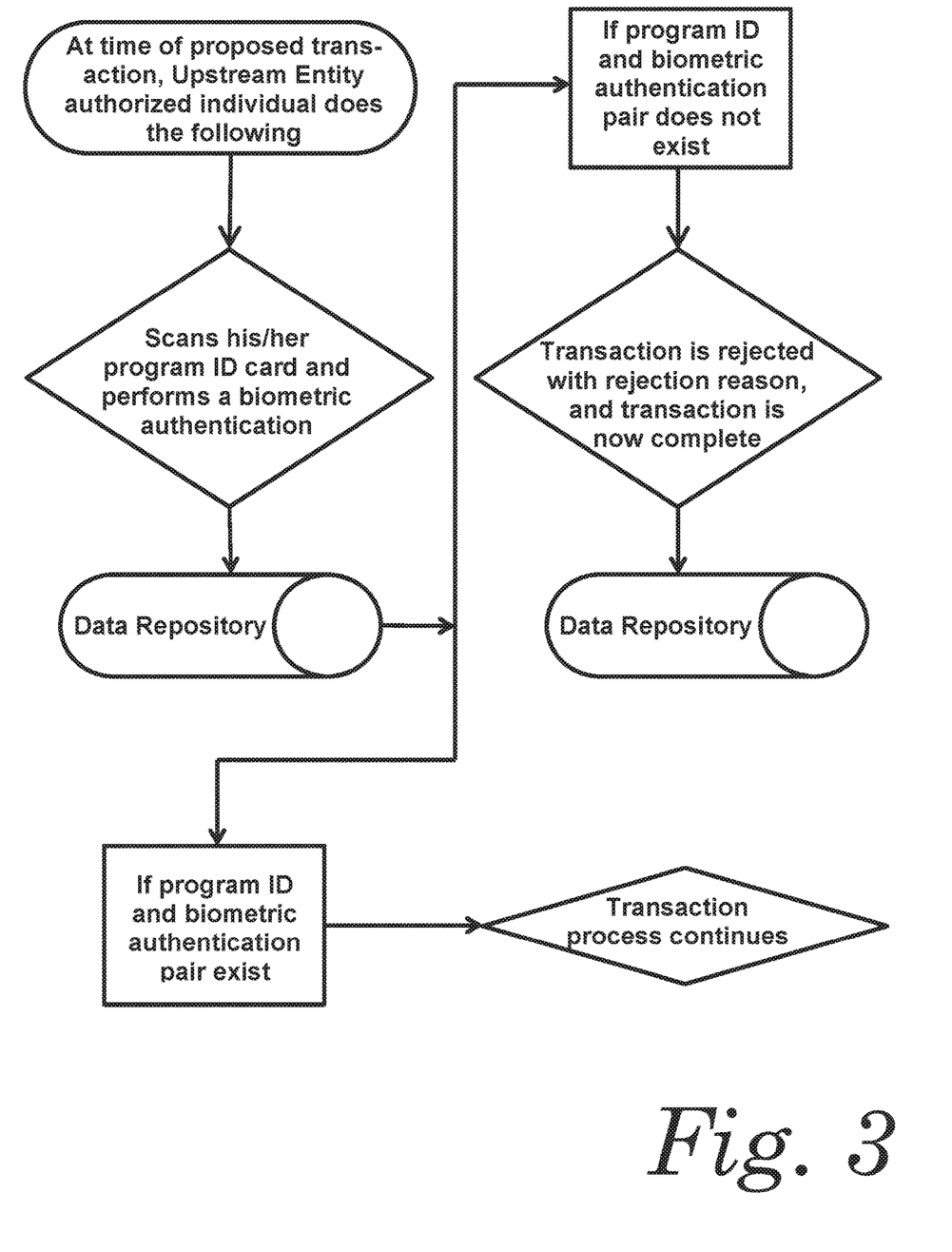
FIG. 3 discloses a distributor-sales transaction in accordance with an embodiment of the present invention.

FIG. 3 discloses a flow chart of an embodiment of the controlled substance sales transaction. For example, a distributor employee, denominated as an "upstream entity authorized individual," may enter, such as by scanning, his or her program identification number and biometric data into the computer-implemented data repository, which either may reject the sale if the number and data do not exist, or allow the sale to continue if the number and data exist.

Figure 4A:
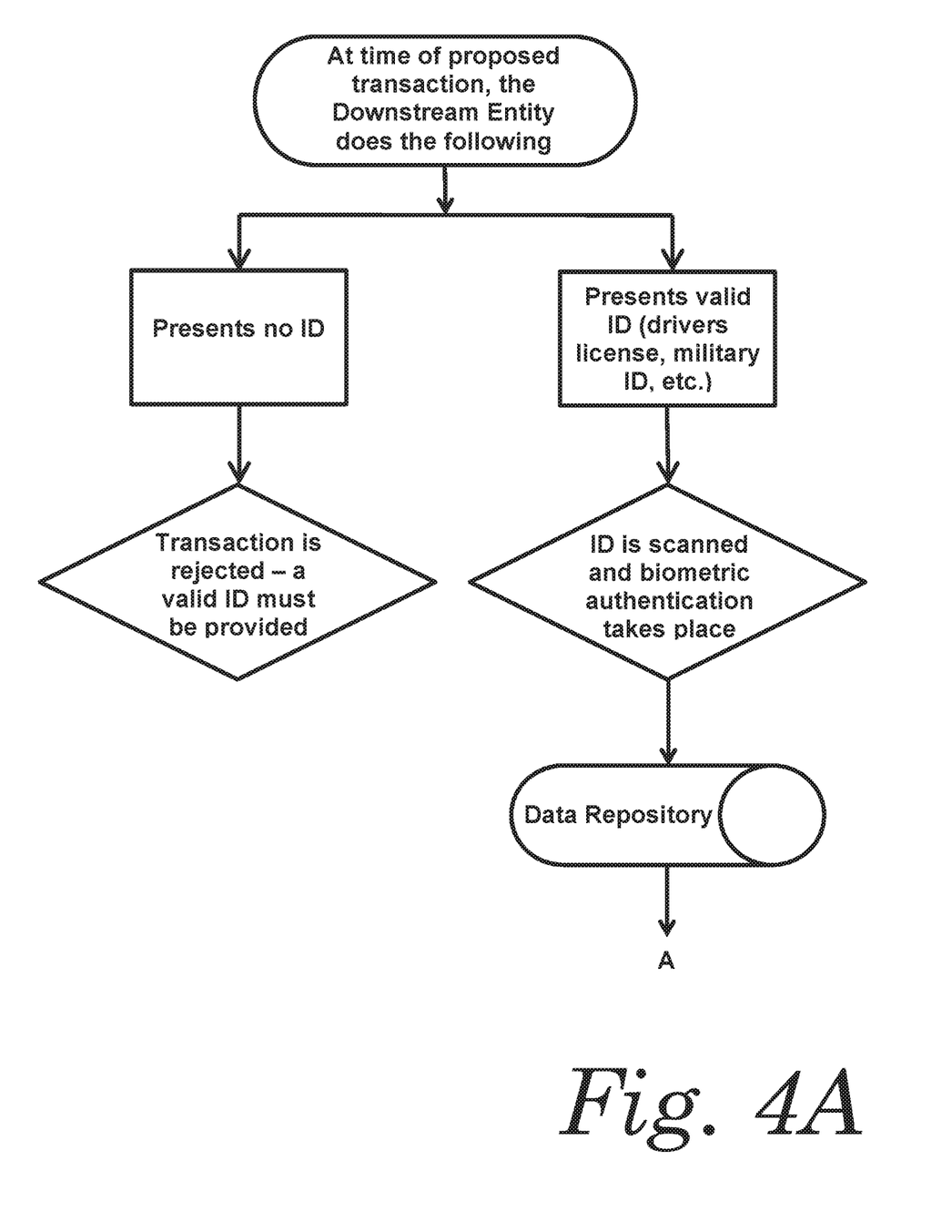
FIG. 4A discloses a first of three series of steps of a recipient-sales transaction in accordance with an embodiment of the present invention.
Figure 4B:
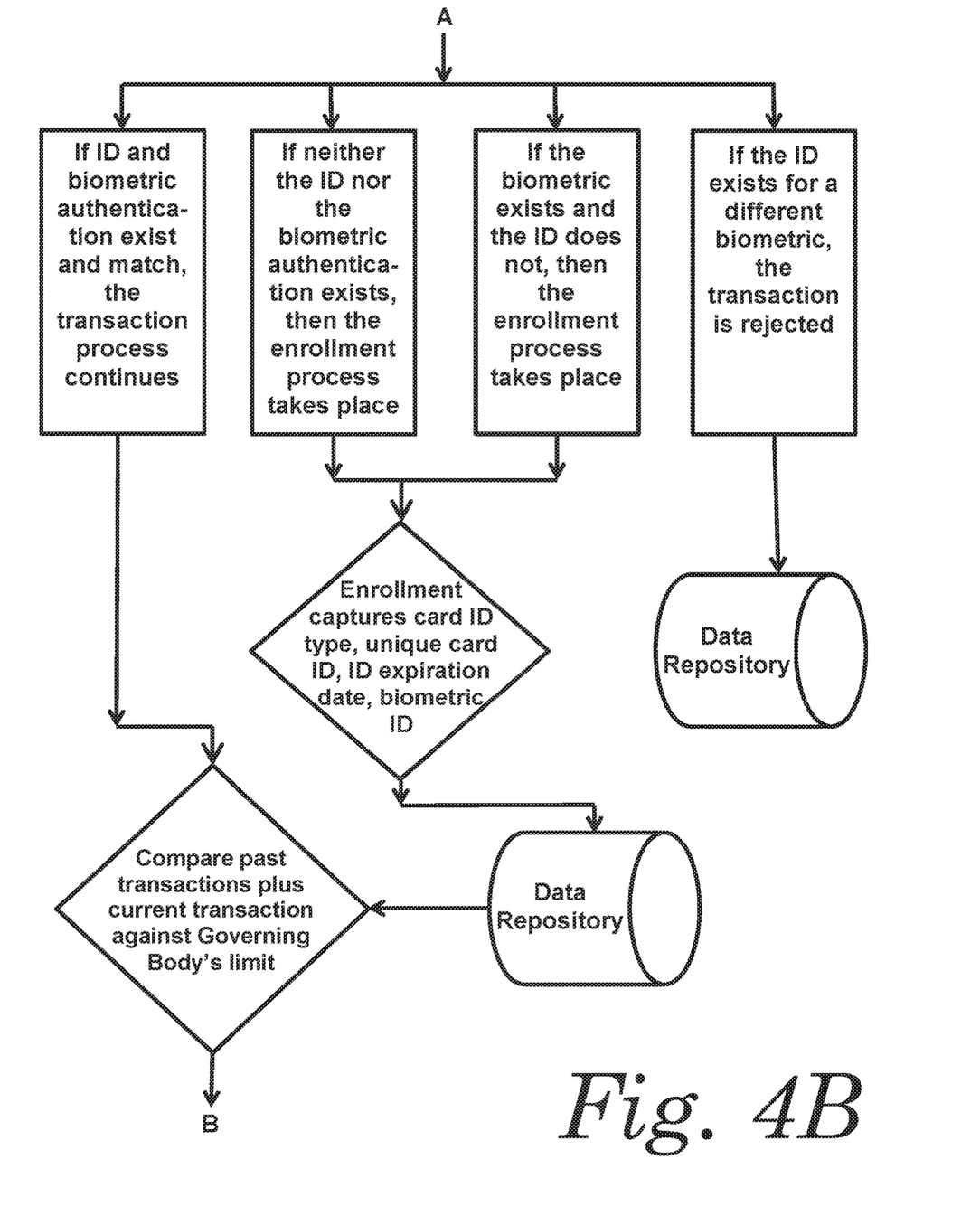
FIG. 4B discloses a second of three series of steps of a recipient-sales transaction in accordance with an embodiment of the present invention.
Figure 4C:
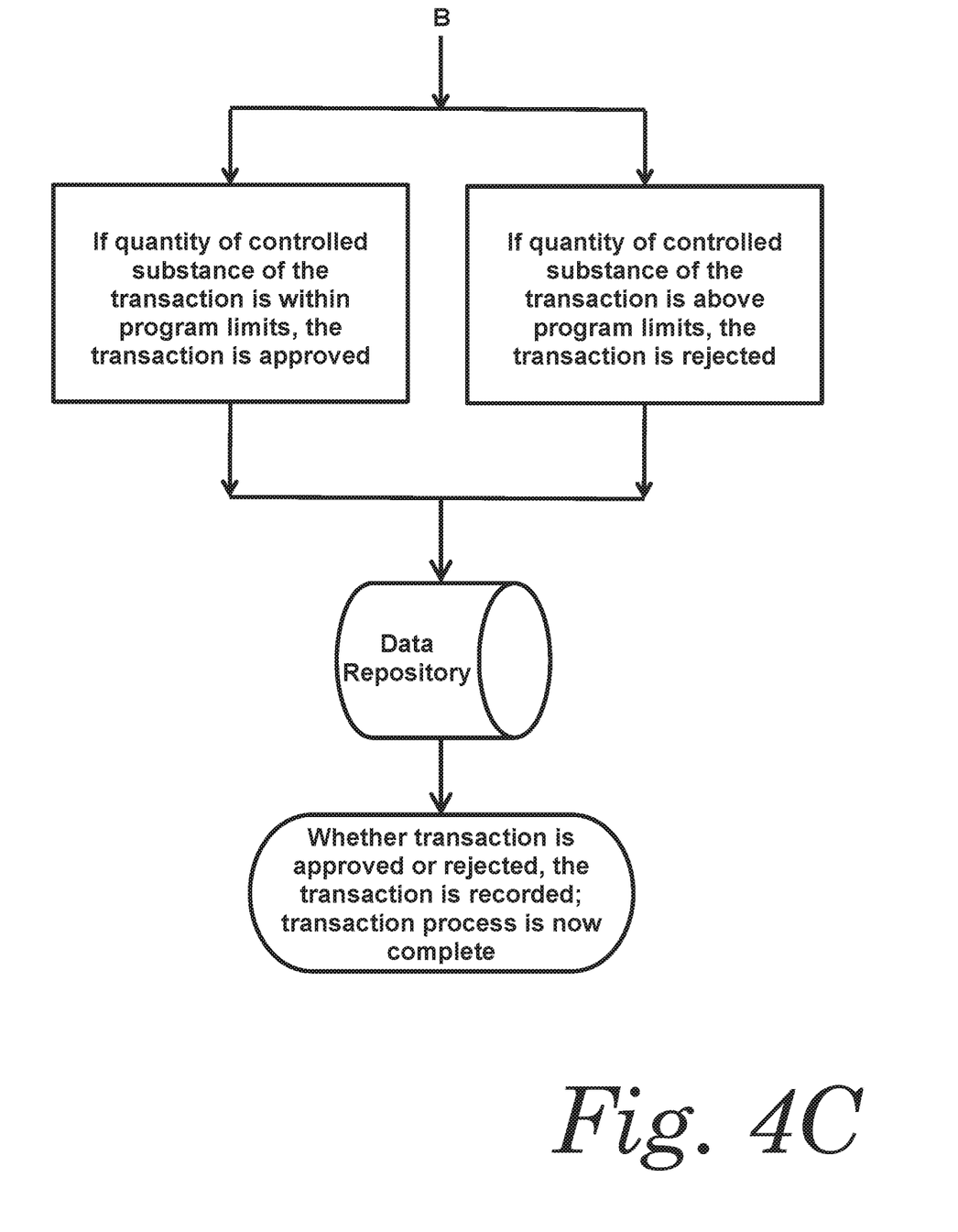
FIG. 4C discloses a third of three series of steps of a recipient-sales transaction in accordance with an embodiment of the present invention.

FIGS. 4A, 4B, and 4C disclose a flow chart of further steps of the controlled substance sales transaction according to an embodiment of the present invention. The sequence of steps illustrated in FIG. 4A continue at Point A to Point A in the sequence of steps illustrated in FIG. 4B, and the sequence of steps illustrated in FIG. 4B continue at Point B to Point B in the sequence of steps illustrated in FIG. 4C. For example, the program identification number and the biometric data of the controlled substance recipient may be entered into the computer-implemented data repository, which either rejects the sale or allows the sale to continue. Only if the program identification number exists and the biometric data matches the corresponding recipient's information may the sale may continue. If the program identification number does not exist and the biometric data does not exist, then the recipient may be enrolled and the sale may continue. If the program identification number does not exist and the biometric data exists, then the recipient may be enrolled and the sale may continue. If the program identification number exists and the biometric data does not match the corresponding recipient, then the sale may be rejected and the attempted transaction may be recorded.

If the sale of the embodiment of FIGS. 4A, 4B, and 4C continues, the amount of controlled substance requested may be entered and summed with the amount of controlled substance the recipient has previously received within a specified time interval. This sum may be compared with the amount the recipient may purchase within a time interval, as established by a governing body. If the sum is less than or equal to the amount of controlled substance the recipient may purchase, the recipient may receive the requested amount of controlled substance. If the sum is not less than or equal to the amount of controlled substance the recipient may purchase, the transaction may be rejected. The outcome of the sales transaction may then be recorded and/or updated in the computer-implemented data repository.

Example

A further example of the detailed steps of an embodiment of the method of the present invention is further described below.

The participants may have two general roles in an exchange. The first role may be a distributor and the second role may be a consumer. The choice of distributor and consumer are merely representative and are used herein to simplify the description of the relationship of the participants, the distributor being an upstream entity and the consumer being a downstream entity. The participants in the disclosed invention may have any relationship where there are members and non-members of a system to monitor who may be mutually and/or securely identified in order to authorize an exchange.

The present invention may utilize one or more forms of identification. The primary form of identification may be referred to as the biometric or other form of secure identification, such as a biometric identification or a Bio ID. The second form of identification may be referred to as a card identification. In one particular embodiment, a card identification for distributors may be referred to as the program identification.

Biometric identification types may include any form of identification related to human characteristics, such as iris pattern recognition, facial recognition patterns, hand prints, fingerprints, retinal scans, and/or any other type of identification chosen as the primary method of identification. The choice of allowable identification types may be based upon the number of authentications needed within a period of time weighed against the false rejection rate predicted for the chosen type of identification.

Card identification types for a distributor may be uniquely identifiable and may represent different levels of access to the authentication system. The identification types that identify distributors in the program may include retail agent, retail owner, regulatory agent, regulatory administrator, and/or any other type of identification chosen as the card identification type.

A consumer card identification may be identified by type of card identification. For those identifications that are issued by a sponsored program, exemplary identification types may include patient, caregiver, resident, and/or any other type of identification type.

Authentication submissions may be defined as enrollment, exchange, or other. Enrollment may occur with a single entity registering, such as entering a biometric identification and/or a card identification for the first time. Enrollment may also occur for a consumer during an exchange or other authentication session. Distributors may complete the enrollment process before they participate in an exchange or other authentication session. For any authentication session where an exchange may be involved, a distributor may be one of the participants. Other participants may include an additional distributor or distributors or a single recipient or multiple recipients.

Exchange types may be receipt, transfer, sale, return, shrinkage, adjustment, and/or waste. The minimum number of participants for any exchange type may be two. An administrative user may have the option to increase the number of participants on any exchange type. This may be used to control exchanges, such as shrinkage, adjustment, and waste. Exchange types may be assigned properties as being between distributors or between a consumer and a distributor. In some embodiments, consumers may only participate in sales and return exchanges with distributors. All other exchange types may occur between two or more distributors.

Sales and return exchange detail may be recorded under the consumer's biometric identification and the exchanges stored for use in determining the eligibility to conduct future exchanges based upon the limits imposed upon the card identification type submitted.

All exchange detail may be held for all exchange types for distributors, which provides an additional method for those monitoring the program to cross-check actual inventories based upon equivalents held by distributors and their assigned station locations.

Distributor enrollment may involve interacting with a biometric identification device and a card identification scanner device via a user interface. When neither the biometric identification nor the card identification exist, they may be registered as a pair, such as if neither one already exists or the card identification has a new expiration date that is later than an existing one for the card identification type.

A new instance with the data repository might be initialized without any pre-loaded card or biometric identifications. It is also possible to load a registry of program identifications and have the biometric identifications populated later via distributor enrollments.

Every physical identification station may have a secure key pair assigned by and stored in the data repository and utilize the key when requesting authentications.

A consumer card identification may go through the single entity enrollment process as it may not be limited to the dual entity exchange process, which may be useful for tracking valued information like arrivals, check-in, check-out, limit queries, and tracking other information.

A distributor may enroll both as a distributor and as a consumer. Based on the card type submitted, such a distributor may be on either side of an exchange. When the presented card type is a consumer type of identification, the presenter may be treated as any other consumer within the system.

For any exchange, if the entity on both sides of the exchange evaluates to the same person, then the exchange may be rejected if the methodology of the present invention is used to perceive an increased possibility of collusion to thwart the goals of the program.

Enrollment services may include distributor enrollment with card identifications issued by a monitored program. The steps of the distributor enrollment may be as follows: Station submits station key, "distenroll", biometric identification, biometric identification type, card identification, card identification type, card data, timestamp; service verifies station key against secure key pair in data repository; if key verification fails, service drops the connection without any response. Otherwise, service checks if the biometric identification exists. If the biometric identification exists, check if the program identification exists. If the program identification does not exist, update the data repository with the card submitted and return a positive response indicating that the card has been added. If the program identification exists for the biometric identification and type, check program identification type and expiration date. If program identification type is different, return a negative response with the identification types and reason. If the identification types are the same and expiration dates are the same, return a positive response and a notice that the identification is already enrolled. If the identification types are the same and the submitted expiration date is later than the existing one, update the data repository and return a positive response indicating that the expiration date has been updated. If the identification types are the same and the submitted expiration date is earlier than the existing one, return a positive response and notice that the submitted expiration date is less that the existing one. If the program identification exists for a different biometric identification of the same biometric identification type, return a negative response and a notice that the identification is already enrolled for a different entity. If the program identification exists for a different biometric identification of a different biometric identification type, verify that it is the same entity and go through the steps above to verify the existing program identification, and based on the results of the verification, return a response based upon that verification. If the program identification exists for a different biometric identification of a different biometric identification type and it is not the same entity, return a negative response and a notice that the identification is already enrolled for a different entity. If the biometric identification does not exist, check if the program identification exists. If the program identification exists, go through the steps above to verify the existing program identification, and based on the results of the verification, additionally update the repository with the biometric identification and type and return a response based upon the program identification verification along with a notice indicating that the biometric identification has been updated. If the program identification does not exist, enroll both the biometric identification and card identification and return a positive response indicating that the enrollment succeeded. Service is completed.

The steps of the consumer enrollment for card identifications not issued by a monitored program may be as follows: station submits station key, "ConsEnroll", biometric identification, biometric identification type, card identification, card identification type, card data, timestamp service verifies station key against secure key pair in data repository. If key verification fails, service drops the connection without any response. Otherwise, service checks if the biometric identification exists. If the biometric identification exists, check if the card identification exists. If the card identification does not exist, update the data repository with the card submitted and return a positive response indicating that the card has been added. If the card identification exists for the biometric identification and type, check card identification type and expiration date. If card identification type is different, return a negative response with the identification types and reason. If the identification types are the same and expiration dates are the same, return a positive response and a notice that the identification is already enrolled. If the identification types are the same and the submitted expiration date is later than the existing one, update the data repository and return a positive response indicating that the expiration date has been updated. If the identification types are the same and the submitted expiration date is earlier than the existing one, return a positive response and notice that the submitted expiration date is less that the existing one. If the card identification exists for a different biometric identification of the same biometric identification type, return a negative response and a notice that the identification is already enrolled for a different entity. If the card identification exists for a different biometric identification of a different biometric identification type, verify that it is the same entity and go through the steps above to verify the existing card identification, and based on the results of the verification, return a response based upon that verification. If the card identification exists for a different biometric identification of a different biometric identification type and it is not the same entity, return a negative response and a notice that the identification is already enrolled for a different entity. If the biometric identification does not exist, check if the card identification exists. If the card identification exists, go through the steps above to verify the existing card identification, and based on the results of the verification, additionally update the repository with the biometric identification and type and return a response based upon the card identification verification along with a notice indicating that the biometric identification has been updated. If the card identification does not exist, enroll both the biometric identification and card identification and return a positive response indicating that the enrollment succeeded. Service is completed.

The steps of consumer enrollment may also be as follows: station submits station key, "PubEnroll", biometric identification, biometric identification type, card identification, card identification type, card data, timestamp service verifies station key against secure key pair in data repository. If key verification fails, service drops the connection without any response otherwise, service checks if the biometric identification exists. If the biometric identification exists, check if the card identification exists. If the card identification does not exist, update the data repository with the card submitted and return a positive response indicating that the card has been added. If the card identification exists for the biometric identification and type, check card identification type and expiration date. If the card identification type is different, return a negative response with the identification types and reason. If the identification types are the same and expiration dates are the same, return a positive response and a notice that the identification is already enrolled. If the identification types are the same and the submitted expiration date is later than the existing one, update the data repository and return a positive response indicating that the expiration date has been updated. If the identification types are the same and the submitted expiration date is earlier than the existing one, return a positive response and a notice that the submitted expiration date is less that the existing one. If the card identification and card type exists for a different biometric identification of the same biometric identification type, return a negative response and a notice that the identification is already enrolled for a different entity. If the card identification and card type exists for a different biometric identification of a different biometric identification type, verify that it is the same entity and go through the steps above to verify the existing card identification, and based on the results of the verification, return a response based upon that verification.

The steps of a sales exchange service may be as follows. If the card identification and card type exists for a different biometric identification of a different biometric identification type and it is not the same entity, return a negative response and a notice that the identification is already enrolled for a different entity. If the biometric identification does not exist, check if the card identification exists. If the card identification and card type exists for the same entity, go through the steps above to verify the existing card id, and based on the results of the verification, additionally update the repository with the biometric identification and type and return a response based upon the card identification verification along with a notice indicating that the biometric identification has been updated. If the card identification does not exist, enroll both the biometric identification and card identification and return a positive response indicating that the enrollment succeeded. Service is completed.

The steps of a returns exchange service may be as follows. Station submits station key, "Return," distributor biometric identification, distributor biometric identification type, distributor card identification, distributor card identification type, distributor card data, consumer biometric identification, consumer biometric identification type, consumer card identification, consumer card identification type, consumer card data, total equivalent amount to be returned, timestamp. Service verifies station key against secure key pair in data repository. If key verification fails, service drops the connection without any response. Distributor combination of distributor biometric identification, distributor biometric identification type, distributor card identification, distributor card identification type is verified. If the verification fails to match all four fields, a negative response is returned indicating that the enrollment for the distributor does not exist. If the verification succeeds, the expiration date is verified to be greater than or equal to the current date. If the card is expired, a negative response is returned indicating that the card for the distributor has expired. At this point, the distributor has been verified. Consumer combination of consumer biometric identification, consumer biometric identification type, consumer card identification, consumer card identification type is verified. If the verification fails to match all four fields, a negative response is returned indicating that the enrollment for the consumer does not exist. If the verification succeeds, the expiration date is verified to be greater than or equal to the current date. If the card is expired, a negative response is returned indicating that the card for the consumer has expired. At this point, the consumer has been verified. The return exchange is recorded with a negative equivalent amount for the consumer and a positive equivalent amount for the distributor and a positive response is returned along with a unique approval code assigned to the exchange. Service is completed.

The steps of a receipt, transfer, shrinkage, and/or waste may be as follows. Station submits station key, ["Receipt-"|"Transfer"|"Shrinkage"|"Waste"] distributor biometric identification, distributor biometric identification type, distributor card identification, distributor card identification type, distributor card data, distributor 2 biometric identification, distributor 2 biometric identification type, distributor 2 card identification, distributor 2 card identification type, distributor 2 card data, total equivalent amount to be transferred from distributor to distributor 2, timestamp[, distributor N biometric identification, distributor N biometric identification type, distributor N card identification, distributor N card identification type, distributor N card data]. Service verifies station key against secure key pair in data repository. If key verification fails, service drops the connection without any response. Distributor 1 combination of distributor biometric identification, distributor biometric identification type, distributor card identification, distributor card identification type is verified. If the verification fails to match all four fields, a negative response is returned indicating that the enrollment for the distributor does not exist. If the verification succeeds, the expiration date is verified to be greater than or equal to the current date. If the card is expired, a negative response is returned indicating that the card for the distributor has expired. At this point, the distributor 1 has been verified. Distributor 2 combination of distributor biometric identification, distributor biometric identification type, distributor card identification, distributor card identification type is verified. If the verification fails to match all 4 fields, a negative response is returned indicating that the enrollment for distributor 2 does not exist. If the verification succeeds, the expiration date is verified to be greater than or equal to the current date. If the card is expired, a negative response is returned indicating that the card for distributor 2 has expired. At this-point, distributor 2 has been verified. Distributor N combination of distributor biometric identification, distributor biometric identification type, distributor card identification, distributor card identification type is verified. If the verification fails to match all four fields, a negative response is returned indicating that the enrollment for the distributor N does not exist. If the verification succeeds, the expiration date is verified to be greater than or equal to the current date. If the card is expired, a negative response is returned indicating that the card for distributor N has expired. At this point, distributor N has been verified. Once all participating distributors have been verified, the transfer from distributor 1 to distributor 2 is recorded as a negative equivalent amount from distributor 1 and a positive equivalent amount to distributor 2 with optional supervision of the exchange by other distributors N. Then a positive response is returned along with a unique approval identification for the exchange. Service is completed.

The steps of other services, such as accessing a consumer limit, may be as follows. Station submits station key, "ConsLimit," distributor biometric identification, distributor biometric identification type, distributor card identification, distributor card identification type, distributor card data, consumer biometric identification, consumer biometric identification type, consumer card identification, consumer card identification type, consumer card data, total equivalent amount to be purchased, timestamp service verifies station key against secure key pair in data repository. If key verification fails, service drops the connection without any response. Distributor combination of distributor biometric identification, distributor biometric identification type, distributor card identification, distributor card identification type is verified. If the verification fails to match all four fields, a negative response is returned indicating that the enrollment for the distributor does not exist. If the verification succeeds, the expiration date is verified to be greater than or equal to the current date. If the card is expired, a negative response is returned indicating that the card for the distributor has expired. At this point, the distributor has been verified. Consumer combination of consumer biometric identification, consumer biometric identification type, consumer card identification, consumer card identification type is verified. Consumer enrollment for the card type is performed. If the response from the enrollment process is negative, the response from the enrollment process is returned. If the response from the enrollment process is positive, the total equivalent amount purchased in the ranges set by the limits set upon the card type is accumulated. A positive response is returned along with the equivalent amount allowance information registered for the card identification type and the accumulated equivalent amounts for the consumer for the range specified for the card identification type used. Service is completed.

Detailed embodiments of the present invention are disclosed herein; however, while various embodiments and examples of this invention have been described above, these descriptions are given for purposes of illustration and explanation, and not limitation. Variations, changes, modifications, and departures from the systems and methods disclosed above may be adopted without departure from the spirit and scope of this invention. Moreover, specific structural and functional details disclosed herein are not to be interpreted as limiting, but merely as a basis for the claims and as a representative basis for teaching one skilled in the art to variously employ the present invention. It will be apparent to those skilled in the art that many changes and substitutions may be made to the foregoing description of preferred embodiments and examples without departing from the spirit and scope of the present invention, which is defined by the appended claims.

Further, the purpose of the Abstract is to enable the various patent offices and the public generally, and especially the scientists, engineers, and practitioners in the art who are not familiar with patent or legal terms or phraseology, to determine quickly from a cursory inspection the nature and essence of the technical disclosure of the application. The Abstract is not intended to be limiting as to the scope of the invention in any way.

The invention claimed is:

1. A method for controlling the transfer of a controlled substance via a network of distributors, the method comprising the steps of:
   providing a computer-implemented data repository for receiving and communicating information, wherein the information includes governing body data, controlled substance distributor data, and controlled substance recipient data;
   providing a governing body to approve distributors to form a network of distributors;
   communicating governing body data including a distinct distributor program identification number for each approved distributor of the network of distributors to the computer-implemented data repository;
   communicating controlled substance distributor data to the computer-implemented data repository, wherein the controlled substance distributor data includes:
      distributor administrator data for each approved distributor, wherein the distributor administrator data includes an administrator program identification number and administrator biometric data; and
      distributor individual data from at least one authorized individual associated with each approved distributor, wherein the distributor individual data includes a stored authorized distributor individual identification number and stored authorized distributor individual biometric data;
   communicating controlled substance recipient data to the computer-implemented data repository, wherein the controlled substance recipient data includes:
      a stored recipient program identification number and stored recipient biometric data from at least one recipient;
      a controlled substance amount limit, wherein the amount limit is a total quantity of the controlled substance the recipient may receive during a predetermined time interval; and
      a controlled substance total, wherein the substance total is a total amount of the controlled substance the recipient has already purchased during the time interval;
   executing a controlled substance transaction for an amount of the controlled substance, wherein the transaction includes:
      providing a controlled substance transaction system for executing services related to the exchange of the controlled substance, the controlled substance transaction system including a first barrier and a second barrier, wherein the first barrier is unlocked upon confirmation of the identity of an authorized individual associated with a distributor and wherein the second barrier is unlocked upon confirmation of an identity of a recipient;
      entering an authorized distributor individual identification number and authorized distributor individual biometric data of the authorized individual associated with a distributor;
      confirming the identity of the authorized individual associated with a distributor by comparing the authorized distributor individual identification number and authorized distributor individual biometric data with the stored authorized distributor individual identification number and stored authorized distributor individual biometric data corresponding to the authorized individual associated with a distributor;
      unlocking the first barrier of the controlled substance transaction system if the authorized distributor individual identification number and authorized distributor individual biometric data match the stored authorized distributor individual identification number and stored authorized distributor individual biometric data corresponding to the authorized individual associated with a distributor;
      entering a first recipient program identification number and a first recipient biometric data of the recipient;
      confirming the identity of the recipient by comparing the first recipient program identification number and the first recipient biometric data with the stored recipient program identification number and stored biometric data corresponding to the recipient;
      unlocking the second barrier of the controlled substance transaction system if the first recipient program identification number and the first recipient biometric data match the stored recipient program identification number and the stored recipient biometric data corresponding to the recipient;

entering a requested amount of the controlled substance;

tracking the weight quantity change of the controlled substance total due to one or more than one of expansion, shrinkage, waste, absorption of ambient humidity, and by drying of the controlled substance over time, and updating the controlled substance total to the computer-implemented data repository;

comparing a sum of the controlled substance total and the requested amount of the controlled substance with the controlled substance amount limit; and transferring the requested amount of the controlled substance to the recipient if the sum is less than or equal to the controlled substance amount limit or rejecting the requested amount of the controlled substance to the recipient if the sum is not less than or equal to the controlled substance amount limit;

updating the controlled substance total in the computer-implemented data repository in view of the controlled substance transaction; and recording the controlled substance transaction in the computer-implemented data repository;

wherein the controlled substance is cannabis based.

2. The method of claim 1 wherein the step of executing a controlled substance transaction further includes the step of enrolling the recipient by generating the first recipient program identification number and the first recipient biometric data and communicating the first recipient program identification number and the first recipient biometric data to the computer-implemented data repository.

3. The method of claim 2 wherein the step of enrolling the recipient further includes generating a unique recipient card with an expiration date and communicating the expiration date and unique recipient card type to the computer-implemented data repository.

4. The method of claim 1 wherein the controlled substance recipient data further includes a unique recipient card with an expiration date.

5. The method of claim 1 wherein the method further includes the step of allowing for return to the distributor of the controlled substance and updating the controlled substance total in the computer-implemented data repository in view of the return of controlled substance.

6. The method of claim 1 wherein the method further includes the step of allowing for tracking of transfer of the controlled substance among distributors between the network of distributors.

7. The method of claim 1 wherein the method further includes the step of allowing for tracking of receipt of the controlled substance between distributors within the network of distributors.

8. The method of claim 1 wherein the method further includes the step of allowing for tracking of waste of the controlled substance.

9. The method of claim 1 wherein the computer-implemented data repository includes the controlled substance transaction system.

10. A method of executing a controlled substance transaction for an amount of a controlled substance, wherein the transaction comprises the steps of:

providing a controlled substance transaction system for executing services related to the exchange of the controlled substance, the controlled substance transaction system including a first barrier and a second barrier, wherein the first barrier is unlocked upon confirmation of an identity of an authorized individual associated with a distributor and wherein the second barrier is unlocked upon confirmation of an identity of a recipient;

entering a first identification number and a first biometric data of the authorized individual associated with a distributor;

confirming the identity of the authorized individual associated with a distributor by comparing the first identification number and the first biometric data with a stored second identification number and a stored second biometric data corresponding to the authorized individual associated with a distributor;

unlocking the first barrier of the controlled substance transaction system if the first identification number and the first biometric data match the stored second identification number and the stored second biometric data corresponding to the authorized individual associated with a distributor;

entering a third identification number and a third biometric data corresponding to a candidate recipient;

confirming the identity of the candidate recipient by comparing the third identification number and the third biometric data with a stored fourth identification number and stored fourth biometric data corresponding to the candidate recipient;

unlocking the second barrier of the controlled substance transaction system if the third identification number and the third biometric data match the stored fourth identification number and the stored fourth biometric data corresponding to the candidate recipient;

entering a requested amount of the controlled substance;

tracking the weight quantity change of the controlled substance total due to one or more than one of expansion, shrinkage, waste, absorption of ambient humidity, and by drying of the controlled substance over time, and updating the controlled substance total;

comparing a sum of the controlled substance total and the requested amount of the controlled substance with the controlled substance amount limit; and transferring the requested amount of the controlled substance to the candidate recipient if the sum is less than or equal to the controlled substance amount limit or rejecting the requested amount of the controlled substance to the candidate recipient if the sum is not less than or equal to the controlled substance amount limit;

wherein the controlled substance is cannabis based.

11. The method of claim 10 wherein the step of executing a controlled substance transaction further includes the step of enrolling the candidate recipient by generating the fourth program identification number and the fourth biometric data and communicating the fourth identification number and the fourth biometric data to the computer-implemented data repository.

12. The method of claim 11 wherein the step of enrolling the candidate recipient further includes generating a unique recipient card with an expiration date and communicating the expiration date and unique recipient card type to the computer-implemented data repository.

13. A method for controlling the dispensing of a controlled substance via a network of distributors, the method comprising the steps of:

providing a computer-implemented data repository for receiving and communicating information, wherein the information includes governing body data, controlled substance distributor data, and controlled substance recipient data;

providing a governing body to approve distributors to form a network of distributors;

communicating governing body data including a distinct distributor program identification number for each approved distributor of the network of distributors to the computer-implemented data repository;

communicating controlled substance distributor data to the computer-implemented data repository, wherein the controlled substance distributor data includes:
distributor administrator data for each approved distributor, wherein the distributor administrator data includes an administrator program identification number and administrator biometric data; and
distributor employee data from at least one employee of each approved distributor, wherein the distributor employee data includes a stored employee identification number and stored employee biometric data;

communicating controlled substance recipient data to the computer-implemented data repository, wherein the controlled substance recipient data includes:
a stored recipient program identification number and stored recipient biometric data from at least one recipient;
a controlled substance amount limit, wherein the amount limit is a total amount of the controlled substance the recipient can receive during a predetermined time interval; and
a controlled substance total, wherein the substance total is a total amount of the controlled substance the recipient has already received during the time interval;

executing a controlled substance transaction between a recipient and a distributor for an amount of the controlled substance;

allowing for return of the controlled substance;

tracking the weight quantity change of the controlled substance total due to one or more than one of expansion, shrinkage, waste, absorption of ambient humidity, and by drying of the controlled substance over time;

updating the controlled substance total and in the computer-implemented data repository in view of the controlled substance transaction; and recording the controlled substance transaction in the computer-implemented data repository;

wherein the controlled substance is cannabis based.

* * * * *